(12) United States Patent
Rock et al.

(10) Patent No.: US 9,078,668 B2
(45) Date of Patent: Jul. 14, 2015

(54) LOCATING A BONE AXIS

(75) Inventors: Mick Rock, Leeds (GB); Callum Colquhoun, Belgrave (AU)

(73) Assignee: DEPUY INTERNATIONAL LIMITED, Leeds (GB)

( * ) Notice: Subject to any disclaimer, the term of this patent is extended or adjusted under 35 U.S.C. 154(b) by 1826 days.

(21) Appl. No.: 12/515,201

(22) PCT Filed: Nov. 8, 2007

(86) PCT No.: PCT/GB2007/004260
§ 371 (c)(1),
(2), (4) Date: Feb. 1, 2010

(87) PCT Pub. No.: WO2008/059211
PCT Pub. Date: May 22, 2008

(65) Prior Publication Data
US 2010/0131021 A1    May 27, 2010

(30) Foreign Application Priority Data

Nov. 15, 2006   (GB) .................................. 0622735.9

(51) Int. Cl.
*A61F 2/46*    (2006.01)
*A61B 17/15*    (2006.01)
*A61B 19/00*    (2006.01)

(52) U.S. Cl.
CPC ......... *A61B 17/155* (2013.01); *A61B 2019/467* (2013.01)

(58) Field of Classification Search
CPC ........................... A61B 17/15; A61B 2019/467
USPC ................. 606/86 R, 87–89, 96–98
See application file for complete search history.

(56) References Cited

U.S. PATENT DOCUMENTS

| 4,952,213 | A | * | 8/1990 | Bowman et al. ................. 606/79 |
| 5,611,353 | A | * | 3/1997 | Dance et al. ................... 600/595 |
| 5,683,397 | A | * | 11/1997 | Vendrely et al. ............... 606/88 |
| 5,709,689 | A | | 1/1998 | Ferrante et al. |
| 5,769,855 | A | * | 6/1998 | Bertin et al. ................... 606/88 |
| 6,629,999 | B1 | * | 10/2003 | Serafin, Jr. .................. 623/20.15 |
| 7,618,421 | B2 | * | 11/2009 | Axelson et al. ................. 606/88 |
| 7,803,158 | B2 | * | 9/2010 | Hayden ........................... 606/80 |

(Continued)

FOREIGN PATENT DOCUMENTS

| EP | 661023 A2 | 7/1995 |
| FR | 2672488 A1 | 8/1992 |

(Continued)

OTHER PUBLICATIONS

PCT International Search Report PCT/GB2007/004260 dated Feb. 18, 2008.

(Continued)

*Primary Examiner* — David Bates
*Assistant Examiner* — Michael Araj

(57) ABSTRACT

A technique for locating an axis of a bone, which extends through the center of rotation of the bone around a joint between that bone and another bone, involves a. moving the bone in a plane about the said joint, between a first point and a second point, b. locating a third point which is equidistant from the first and second points, and c. locating the axis which passes through the third point, perpendicular to a line which connects the first and second points. The invention provides an instrument for performing this technique.

5 Claims, 3 Drawing Sheets

(56) References Cited

U.S. PATENT DOCUMENTS

| | | | |
|---|---|---|---|
| 7,862,570 B2 * | 1/2011 | Russell et al. | 606/87 |
| 2002/0133162 A1 | 9/2002 | Axelson | |
| 2005/0015022 A1 * | 1/2005 | Richard et al. | 600/587 |
| 2006/0004284 A1 * | 1/2006 | Grunschlager et al. | 600/416 |
| 2006/0015120 A1 * | 1/2006 | Richard et al. | 606/102 |

FOREIGN PATENT DOCUMENTS

| | | |
|---|---|---|
| FR | 2684870 A1 | 6/1993 |
| WO | WO 9925263 | 5/1999 |
| WO | WO 0100096 | 1/2001 |
| WO | WO 2005007004 | 1/2005 |

OTHER PUBLICATIONS

UK Search Report GB0622735.9—search dated Feb. 15, 2007.
Hermann, T.; Femoral Prosthesis Positioning Instrument; FR 2672488A1 English Abstract; Aug. 14, 1992; Derwent World Patents Index; © 2009 Derwent Information Ltd. All rights reserved. Dialog® File No. 351 Accession No. 6094203.
Charpenet, R. et al; Method for Determining the Knee Entry Point—Using Femur Intra-Medullary Probe to Measure Distance; FR 2684870A1 English Abstract Jun. 18, 1993; Derwent World Patents Index; © 2009 Derwent Information Ltd. All rights reserved. Dialog® File No. 351 Accession No. 6484077.

* cited by examiner

LOCATING A BONE AXIS

This invention relates to the location of an axis of a bone which extends through the centre of rotation of the bone around a joint between that bone and another bone. The invention provides a method of locating a bone axis and an instrument for locating a bone axis.

The anatomic and mechanical axes of certain bones do not coincide. The anatomic axis is defined by the bone tissue itself where it extends along the length of the bone. The anatomic axis can be located by means of an intra-medullary rod, or by means of an extra-medullary instrument which can be fixed to the bone at spaced apart points. The mechanical axis can deviate from the anatomic axis. For example, in the case of the femur, the mechanical axis extends from the centre of the femoral head where it is received in the acetabulum, to the notch between the condyles which engage the tibia.

It can be important to locate the mechanical axis of a bone, for example in a surgical procedure to prepare that bone to receive an implant such as a component of a joint prosthesis. For example, the distal end of a femur should be resected to receive the femoral component of a knee joint prosthesis. The orientation of the resection planes should be defined with respect to the mechanical axis of the femur.

It is known to locate the mechanical axis of the femur using pre-operative images of the femur, which can be used to determine the relationship between the anatomic and mechanical axis. During the course of the surgical procedure, the anatomic axis can be determined using an intra-medullary rod. This can be used to determine the mechanical axis with reference to the pre-operative image data.

The present invention provides a technique for locating the mechanical axis of a bone without use of an intra-medullary rod, by manipulating the joint between the bone and another bone.

Accordingly, in one aspect, the invention provides a method of locating an axis of a bone which extends through the centre of rotation of the bone around a joint between that bone and another bone, which comprises:
 a. moving the bone in a plane about the said joint, between a first point and a second point,
 b. locating a third point which is equidistant from the first and second points, and
 c. locating the axis which passes through the third point, perpendicular to a line which connects the first and second points.

The axis itself can be located and identified, for example being traced from the end of the bone which is remote from the joint between the bone and another bone, to the centre of rotation. The information about the location of the axis (passing through the third point) and its orientation (perpendicular to a line which connects the first and second points) can be used to place other instruments which might be used in a surgical procedure without necessarily tracing the axis from the end of the bone which is remote from the joint between the bone and another bone, to the centre of rotation.

In another aspect, the invention provides an instrument for locating an axis of a bone which extends through the centre of rotation of the bone around a joint between that bone and another bone, which comprises:
 a. a support,
 b. a marker component for fitting to the support at first point, for engaging the bone in a predetermined position thereon when the bone is located adjacent to the first point, to locate the first end of the support relative to the bone,
 c. a marker component for fitting to the support at a second point, for engaging the bone in a predetermined position thereon when the bone is moved from its position adjacent to the first point and is located adjacent to the second point, to locate the second point on the support relative to the bone,
 d. a marker component for fitting to the support at a point which is midway between the first and second points, for engaging the bone in a predetermined position thereon when the bone is in a position which is between its positions adjacent to the first and second points on the support, and
 e. a clamp for fixing the position of the support against movement after the first and second points thereon have been located relative to the bone.

The technique which is provided by the present invention has the advantage in some embodiments that it enables the mechanical axis of a bone to be determined without having to use an intra-medullary rod. The technique which is provided by the present invention has the advantage in some embodiments that it enables the mechanical axis of a bone to be determined without having to make an incision, provided that the marker component can be engaged appropriately with an appropriate landmark, for example on a patient's bone through overlying tissue. The mechanical axis of the bone can be determined simply by manipulating the bone, preferably making use of the instrument of the present invention.

The method of the invention does not need to be performed by a medical practitioner. For example, it can be performed by a technician. The method of the invention does not need to be performed as part of a surgical procedure.

The technique of the present invention can be applied to bones for which the anatomic axis coincides with the mechanical axis. The technique of the present invention finds particular application when the mechanical axis and the anatomic axis do not coincide. For example, the technique of the present invention can be used in relation to a femur.

It will generally be preferred for the first and second points to be located with reference to a landmark on the bone which lies on the axis which is to be located. For example, when the bone is a femur, each of the first and second points can be located with reference to the inter-condylar notch.

Preferably, the method of the invention is performed using an instrument which comprises a support, having (a) predetermined first and second features thereon which can be located in relation to the first and second points, and (b) a marker on the support to identify the third point.

The support which is used in the invention should define first and second points so that the third point can be located as required relative to the first and second features. The support can be in the form of a bar on which the first and second features can be identified, for example by visible markings or formations in the form of protuberances or detents. The support can be in the form of a frame. For example, the support can be provided as four members which are connected to one another to form a quadrilateral, with the length of the adjacent members of a first pair being equal, and the length of the adjacent members of a second pair being equal. The first and second points is then defined relative to the connections between a member of the first pair and a member of the second pair. The mechanical axis of the bone is then defined by a line which joins the connections between the members of first pair and the members of the second pair, with the third point lying on that line.

The instrument can include an axis rod which extends perpendicularly to the line which joins the first and second points at the third point. For example, when the support is provided in the form of a bar, an axis rod can be connected to the bar at the third point.

The axis rod provides the user with an indication of the orientation of the axis where it extends from the point on the bar which is midway between the first and second points.

Preferably, the instrument includes at least one marker component which extends from the support at at least one of the first, second and third points in a direction towards the bone, to contact the bone to locate it relative to the support.

Preferably, in performing a method of the invention, the bone is moved between the first and second positions through an angle of at least about 30°.

Either or each of the first and second points on the bar can be located at or towards respective ends of the bar. This can have the advantage of providing a ready point of reference as to the location of the points. The first and second points can be defined by stops which limit the movement of an element along the bar between the first and second points. Such stops might be formed by a protuberance on one or more surfaces of the bar. One or each of the first and second points might be provided by a detent into which a resilient member on a sliding element can be received as an element is slid along the bar towards the detent. Points on the bar might also be defined by means of holes (which can be blind or can extend entirely through the bar) which can receive a retractable locking pin on a sliding member.

It can be preferred for a common marker component to be fitted to the support of the instrument of the invention at both its first point and its second point. For example, a marker component can be fitted to an element which can slide along the bar between the first and second points. It can also be preferred for separate first and second marker components to be provided, for fitting to the bar at the first and second points respectively.

The or each marker component which is provided on the support to extend towards the bone at at least one of the first, second and third points can be in the form of a pin. The marker component should be appropriately dimensioned to engage the bone, for example directly or through overlying tissue. The marker component should extend sufficiently from the support to enable appropriate referencing relative to the bone to be performed, especially so that the marker component engages the bone. When the marker component is intended to engage a recess on the bone, the end of the marker component should be appropriately dimensioned so that it will fit into the recess (for example the inter-condylar notch on the femur). Preferably, when the marker component comprises a pin, the pin should be arranged so that it can slide relative to the support to adjust the effective length of the pin which extends from the support towards the bone.

Preferably, the clamp includes a stand which extends upwardly from the surface on which the patient lies when the instrument is in use, to which the support can be connected, directly or indirectly. The stand can be fastened to an appropriate structure, for example a rail on the operating table. Alternatively, the clamp can include a heavy base for the stand, whose mass is such that, once placed on an operating table, it resists accidental displacement.

The clamp should preferably be capable of fixing separately the first and second ends of the support against movement. For example, it can be preferred to locate the bone relative to the first point of the support, and then clamp the support so that the first point is fixed against movement. The bone should then be moved so that it is located adjacent the second point on the support. The support should then be fixed to prevent movement of the second point.

The clamp can allow translation of the support or rotation of the support or both, for example relative to the stand. Clamps which can be used to fasten a support against translation or rotation or both are known. Such clamps can suitably be engaged by means of a threaded actuator, for example which can draw two members together to grip the support. Other clamping arrangements which can be used are known, for example from surgical instruments, and from other type of technical apparatus such as laboratory equipment.

The instrument of the present invention will generally be made from metals. Suitable metals for use in the construction of medical instruments are preferred, especially certain stainless steels. The instrument of the invention can be made from other materials such as polymeric materials, or from combinations of different materials, for example combinations of polymeric and metallic materials.

The instrument of the invention can be configured to have fixed to it another instrument component for use in a surgical procedure. For example, the instrument of the invention can be used with a cutting block which can be used in a resection step of a surgical procedure. Accordingly, in other aspect, the invention provides a kit which includes an instrument as discussed above, together with a cutting block for use in a resection step of a surgical procedure.

The kit of the invention has the advantage that the orientation of the resection plane can be referenced relative to the mechanical axis of the bone which is determined using the instrument of the invention.

The support can have formations for fastening the cutting block. For example, the support can have holes formed in it which can receive fasteners for fastening the cutting block to the support. It is also envisaged that, once the cutting block has been located on the support, its position or orientation or both can be adjusted, for example to adjust the angle of the resection plane to the mechanical axis of the bone, or to adjust the position of the resection plane along the mechanical axis of the bone. It can be appropriate for example to set the position of the resection plane along the mechanical axis of the bone with reference to an anatomical landmark. When an incision has been made in the vicinity of a bone joint, the position of the resection plane along the mechanical axis of the bone might be set with reference to the end face of the bone.

The support can have formations which define the location and orientation of pins which can be used subsequently (for example after removal of the support) to locate a cutting block. For example, such formations might be in the form of bores which extend through the support, through which pins can be inserted into the patient's bone.

Embodiments of the present invention will now be described by way of example with reference to the accompanying drawings, in which.

Figure 1:
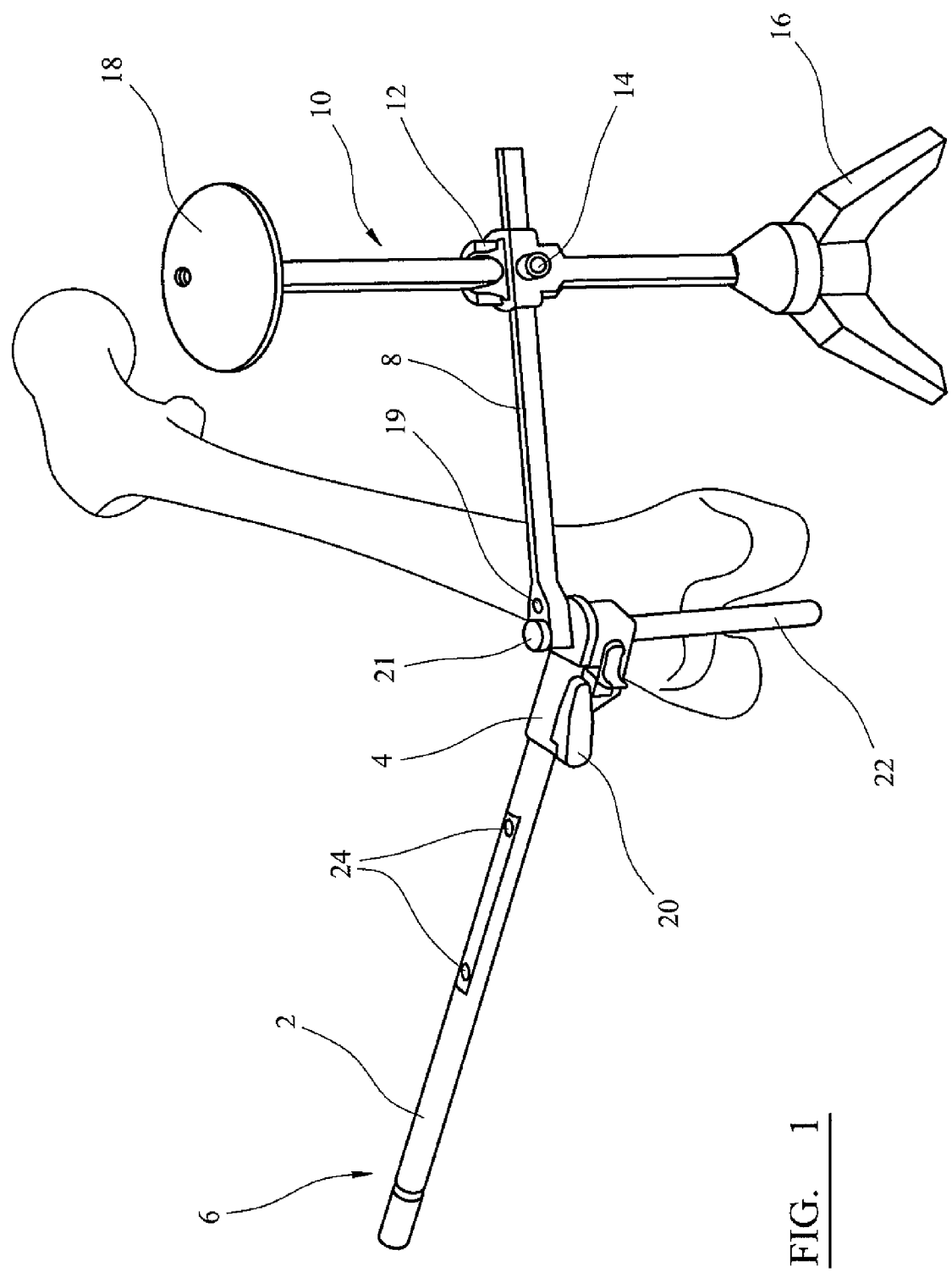
FIG. 1 shows the instrument of the invention, together with a simulation of a patient's femur.

Referring to the drawings, FIG. 1 shows the instrument of the invention which comprises a bar 2 which has a slider 4 mounted. As shown in FIG. 1, the slider is located at a first point towards one end of the bar. The slider can be slid to second point 6 at the other end of the bar.

The instrument includes a stand 10, having a connector arm 8 extending between the stand and the bar. The connector arm is connected to the stand by means of a clamp 12. The height of the connector arm and of the bar on the stand can be adjusted, and fixed against movement by means of a threaded fastener 14 which forms part of the connector. The connector arm is also arranged for rotation around the axis of the stand when the threaded fastener 14 is loosened. In this way, the first end of the bar can be located as desired. The stand has a stable tripod base 16, and a handhold 18 at its upper end so that a user can hold the stand in a stable position.

The slider 4 can be restrained against sliding movement along the bar 2 by means of a sprung trigger fastener 20 which can engage detents in the side wall of the bar. The slider might be clamped against sliding movement by means of a threaded fastener. The slider has a rod 22 extending vertically from it. The rod is shaped so as to be a snug fit in the inter-condylar notch of a patient's femur.

The bar 2 has a pair of holes 24 in its upper face. These can be used to receive fasteners (for example pins or threaded screws) for fastening a cutting block to the bar. Such pins might be used to locate a cutting block which has holes formed in it in which the pins can be received.

Figure 2:
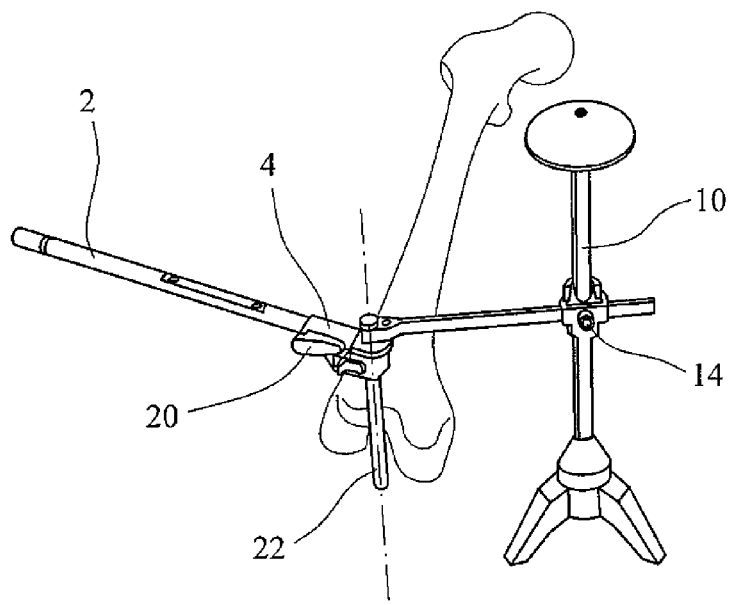
FIGS. 2 to 4 illustrate use of the instrument of the invention in a method for locating the mechanical axis of a patient's femur.
Figure 3:
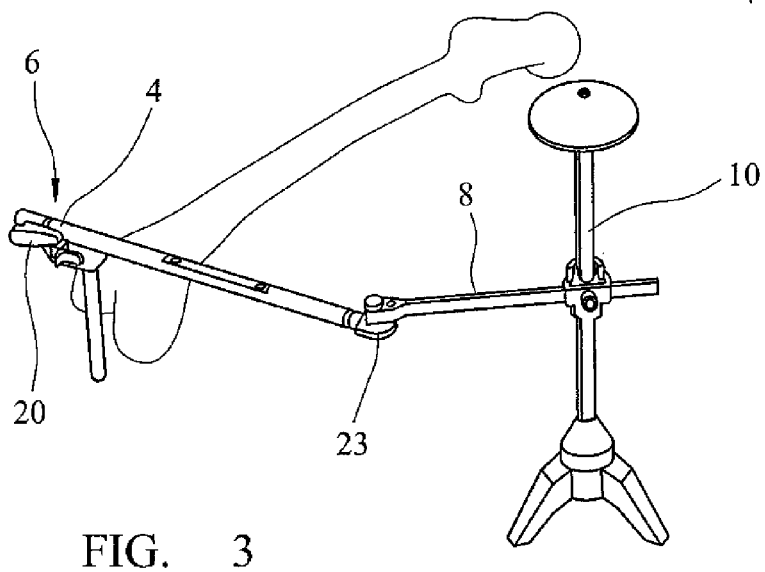
Figure 4:
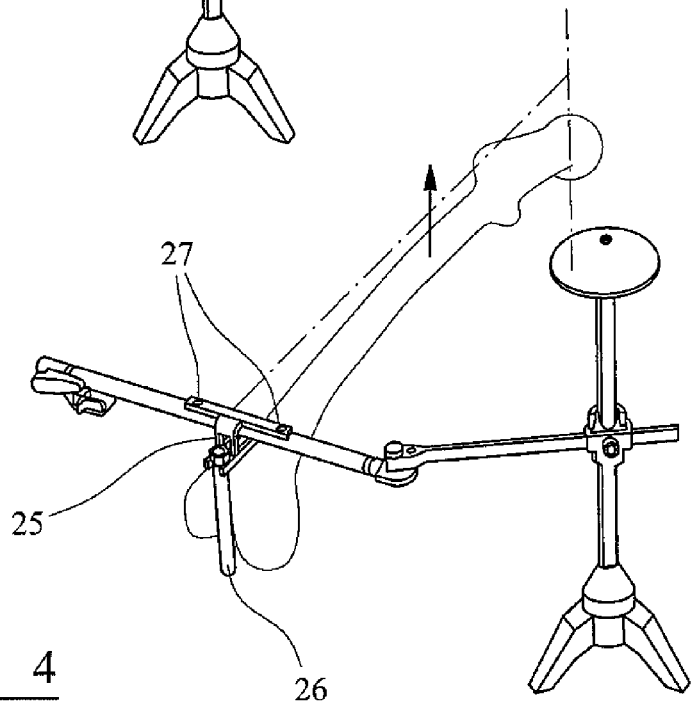

Use of the instrument of the invention in a procedure for locating the femoral axis of a femur is illustrated in FIGS. 2 to 4.

In a first step, as shown in FIG. 2, the slider 4 is located at a first end of the bar 2 and clamped in position. With the femur rotated medially through an angle of about 15°, the rod 22 is located in the inter-condylar notch, either by moving the stand, or by moving the connector arm, relative to the stand once the fastener 14 has been loosened. When the rod 22 is located in the inter-condylar notch, the first end of the bar and the rod are clamped against further movement and the stand is stabilised against further movement.

The femur is then rotated laterally through an angle of about 30° as shown in FIG. 3. After releasing the fastener 20, the slider 4 is slid until the rod engages again the inter-condylar notch. This might require loosening the joint 23 between the connector arm and the bar. When the rod has been located securely in the inter-condylar notch, the joint between the connector arm and the bar is tightened. The joint between the connector arm and the bar can be provided by a pivot pin 21 (which is visible in FIG. 1) which about which the connector arm or the bar or each of them can pivot. The joint can be tightened by means of a screw which extends through a threaded bore 19 in the connector arm and impinges on the top face of the bar when tightened.

FIG. 4 shows the femur after it has been rotated through an angle of about 15°, so that the distal end of the femur is located approximately midway between the first and second ends of the bar 2. A marker component 25 is located at the midpoint of the bar, where it is located by means of a pair of fastener pins 27 which are received in the holes 24 in the bar. The marker component includes a rod 26 which can be located in the inter-condylar notch.

Figure 5A:
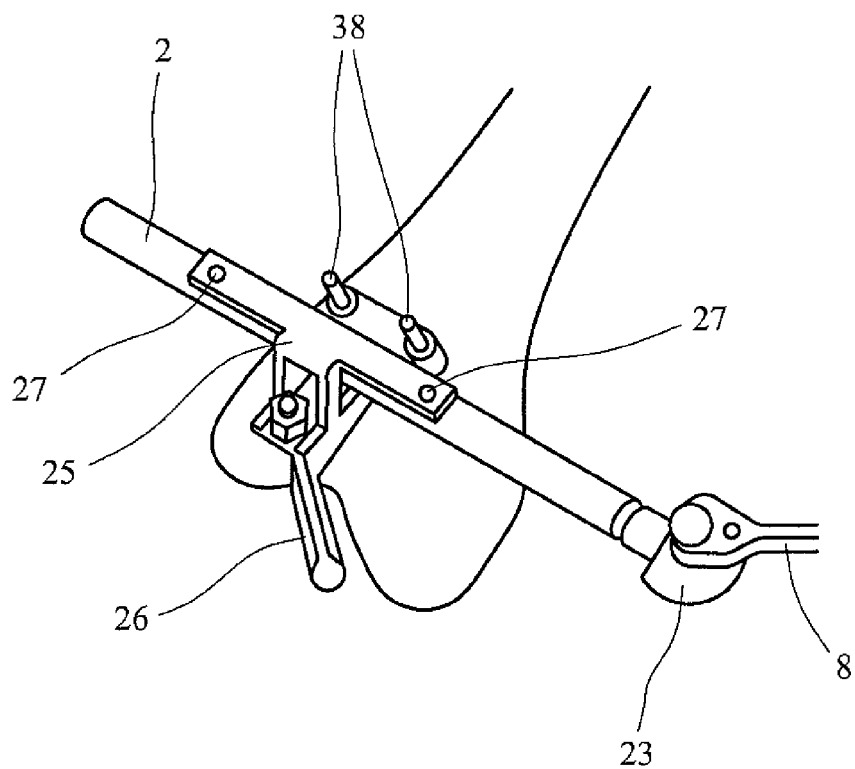
FIG. 5a is an enlarged view of the distal end of the femur shown in FIG. 4, located relative to the point on the bar which is mid-way between the first and second points.

FIG. 5a is an enlarged view of the bar 2 having a marker component 25 for the third point fitted to it. The marker component can be fastened to the bar using a pair of fastener pins 27, which can be received in the holes 24 which are provided in the bar.

The marker component has a rod 26 extending from it, and defines a pair of pin holes. In use, the marker component is fitted to the bar with the rod received in the inter-condylar notch. Pins 38 are then inserted into the holes so that the location of the pins in the bone is controlled relative to the mechanical axis of the femur.

Figure 5B:
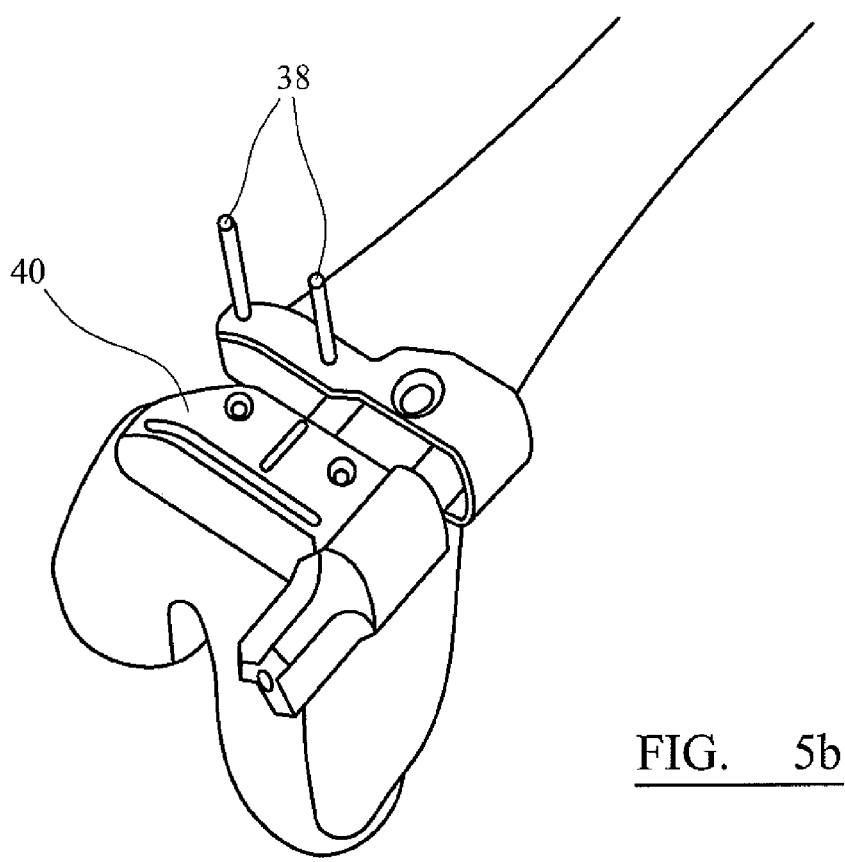
FIG. 5b is an isometric view of the distal end of the femur, with a cutting block located on it.

In a subsequent step as shown in FIG. 5b, a cutting guide 40 can be located on the bone using the pins 38 which have previously been inserted into the bone.

The invention claimed is:

1. A method of defining an axis of a first bone that extends through a center of rotation of the first bone around a joint between the first bone and a second bone so that a resection plane defined by a cutting guide may be referenced relative to the mechanical axis of the bone, the method comprising the steps of:
   moving the first bone in a plane about the joint, between a first point and a second point;
   defining a third point that is equidistant from the first and second points;
   defining the axis that passes through the third point, perpendicular to a line that connects the first and second points, wherein the bone is a femur having a distal end having an inter-condylar notch, and wherein each of the first and second points is located with reference to the inter-condylar notch;
   using an instrument that includes a support with (a) predetermined first and second features thereon that can be located in relation to the first and second points, and (b) a marker thereon to identify the third point;
   moving the femur to a position wherein the distal end of the femur is between the first and second points;
   setting reference elements at locations in the bone that are controlled relative to the defined axis; and
   attaching a cutting guide to the reference elements.

2. The method of claim 1, further comprising the step of tracing the axis from the end of the bone that is remote from the joint to the center of rotation.

3. The method of claim 1, wherein the instrument includes an axis rod that extends perpendicularly from the support at the third point.

4. The method of claim 1, wherein the instrument includes at least one marker component that extends from the support of at least one of the first, second and third points in a direction towards the bone, to contact the bone to locate the bone relative to the support.

5. The method of claim 1, wherein the angle through which the bone is moved between the first and second points is at least about 30 degrees.

\* \* \* \* \*